(12) United States Patent
Stepanek et al.

(10) Patent No.: US 11,529,492 B2
(45) Date of Patent: Dec. 20, 2022

(54) METHODS AND MATERIALS FOR TREATING HYPOCAPNIA

(71) Applicant: Mayo Foundation for Medical Education and Research, Rochester, MN (US)

(72) Inventors: Jan Stepanek, Scottsdale, AZ (US); Michael J. Cevette, Cave Creek, AZ (US); Gaurav N. Pradhan, Fountain Hills, AZ (US); Karen K. Breznak, Rio Verde, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 436 days.

(21) Appl. No.: 16/624,398

(22) PCT Filed: Jun. 28, 2018

(86) PCT No.: PCT/US2018/039959
§ 371 (c)(1),
(2) Date: Dec. 19, 2019

(87) PCT Pub. No.: WO2019/006096
PCT Pub. Date: Jan. 3, 2019

(65) Prior Publication Data
US 2020/0121875 A1   Apr. 23, 2020

Related U.S. Application Data

(60) Provisional application No. 62/671,817, filed on May 15, 2018, provisional application No. 62/625,103, (Continued)

(51) Int. Cl.
  A61M 16/12 (2006.01)
  A61M 16/00 (2006.01)
  A61M 16/06 (2006.01)

(52) U.S. Cl.
  CPC ........ *A61M 16/12* (2013.01); *A61M 16/0045* (2013.01); *A61M 16/06* (2013.01);
  (Continued)

(58) Field of Classification Search
  CPC ...... A61M 16/00; A61M 16/06; A61M 16/10; A61M 16/1005; A61M 16/101;
  (Continued)

(56) References Cited

U.S. PATENT DOCUMENTS 3,361,631 A   1/1968   Weinstein
3,776,227 A   12/1973  Pitesky et al.
(Continued)

FOREIGN PATENT DOCUMENTS

EP        0737473       10/1996
WO   WO 1993/023102   11/1993
(Continued)

OTHER PUBLICATIONS

Akça et al., "Effect of intra-operative end-tidal carbon dioxide partial pressure on tissue oxygenation," Anaesthesia, 58(6):536-42, Jun. 2003.
(Continued)

*Primary Examiner* — Joseph D. Boecker
(74) *Attorney, Agent, or Firm* — Fish & Richardson P.C.

(57) ABSTRACT

This document provides methods and materials for treating hypocapnia. For example, methods and materials for delivering $CO_2$ to a mammal to treat hypocapnia or compensate for a reduced level of $CO_2$ are provided.

16 Claims, 10 Drawing Sheets

Related U.S. Application Data filed on Feb. 1, 2018, provisional application No. 62/526,181, filed on Jun. 28, 2017.

(52) U.S. Cl.
CPC ............... *A61M 2202/0208* (2013.01); *A61M 2202/0225* (2013.01)

(58) Field of Classification Search
CPC ............ A61M 16/12; A61M 2016/103; A61M 2202/0225; A61M 13/00; A61M 13/003; A62B 7/08; A62B 7/14; A62B 21/00
See application file for complete search history.

(56) References Cited

U.S. PATENT DOCUMENTS

| | | | |
|---|---|---|---|
| 4,289,794 A | 9/1981 | Kleiner et al. | |
| 4,615,923 A | 10/1986 | Marx | |
| 4,639,368 A | 1/1987 | Niazi et al. | |
| 8,602,789 B2 | 12/2013 | Hallowell et al. | |
| 2001/0037810 A1* | 11/2001 | Fine | A61K 33/00 128/203.26 |
| 2002/0096174 A1* | 7/2002 | Hill | A61M 16/10 128/204.22 |
| 2004/0255939 A1 | 12/2004 | Feldman | |
| 2005/0061323 A1 | 3/2005 | Lee et al. | |
| 2005/0245307 A1 | 11/2005 | Gatto et al. | |
| 2005/0279350 A1* | 12/2005 | Rasor | A61P 37/08 128/200.14 |
| 2006/0048779 A1* | 3/2006 | Rounbehler | A61P 11/06 128/203.12 |
| 2009/0171268 A1* | 7/2009 | Williams, Jr. | A61M 13/003 604/26 |
| 2010/0034871 A1 | 2/2010 | Mikkelsen et al. | |
| 2011/0300216 A1 | 12/2011 | First et al. | |
| 2012/0060933 A1* | 3/2012 | Frembgen | A61M 16/00 205/555 |
| 2012/0150545 A1 | 6/2012 | Simon | |
| 2012/0238831 A1 | 9/2012 | Benford | |
| 2012/0279498 A1 | 11/2012 | Nakamura | |
| 2014/0081169 A1* | 3/2014 | Gerding | A61K 31/194 600/560 |
| 2014/0154650 A1 | 6/2014 | Stack | |
| 2014/0199670 A1 | 7/2014 | Stack | |
| 2014/0227202 A1 | 8/2014 | Pilgaonkar et al. | |
| 2014/0352521 A1 | 12/2014 | Takahashi et al. | |
| 2015/0045725 A1* | 2/2015 | Smith | A61B 1/31 604/26 |
| 2015/0320350 A1 | 11/2015 | Ishikawa et al. | |
| 2015/0367087 A1* | 12/2015 | Dor Zidon | A61M 13/003 604/26 |
| 2016/0213298 A1 | 7/2016 | Elsmore et al. | |
| 2016/0302713 A1 | 10/2016 | Maruta et al. | |
| 2016/0367442 A1 | 12/2016 | Baker | |
| 2017/0333664 A1* | 11/2017 | Luo | A61B 5/316 |
| 2019/0099566 A1* | 4/2019 | Gramann | A61M 11/02 |
| 2019/0259291 A1 | 8/2019 | Pradhan | |

FOREIGN PATENT DOCUMENTS

| | | | |
|---|---|---|---|
| WO | WO 2001/003645 | 1/2001 | |
| WO | WO 2001/005445 | 1/2001 | |
| WO | WO-0105445 A2 * | 1/2001 | ............. A61L 15/42 |
| WO | WO 2016/073582 | 5/2016 | |
| WO | WO 2016/102450 | 6/2016 | |

OTHER PUBLICATIONS

Akça et al., "Hypercapnia improves tissue oxygenation," Anesthesiology: The Journal of the American Society of Anesthesiologists, 97(4):801-6, Oct. 2002.
Almajidi and Maraie, "An Overview on Oroslippery Technique as A Promising Alternative for Tablets used in Dysphagia," Research Journal of Pharmacy and Technology, 2019, 12(9):4545-9.
BioMed Central [online], "Bicarbonate adds fizz to players' tennis performance," Oct. 27, 2010, [retrieved on Sep. 24, 2020] retrieved from: URL<www.sciencedaily.com/releases/2010/10/101025221739.htm>, 3 pages.
Boothby, Chapter 10 from "Respiratory Physiology in Aviation", Editor W.M. Boothby, MD, The Lovelace Foundation for Medical Education and Research, Albuquerque, NM; Air University, USAF School of Aviation Medicine, Randolph Field, TX, Sep. 1954.
Brogan et al., "Pulmonary NO synthase inhibition and inspired CO2: effects on V'/Q' and pulmonary blood flow distribution," European Respiratory Journal, Aug. 2000, 16(2):288-95.
Brzecka, "Role of hypercapnia in brain oxygenation in sleep-disordered breathing," Acta neurobiologiae experimentalis, Jan. 2007, 67(2):197.
Candyblog.net [online], "Candy Blog: Pop Rocks," dated Sep. 27, 2007, [retrieved on Sep. 24, 2020], retrieved from: URL<http://www.candyblog.net/blog/category/poprocks/>, 6 pages.
Chen and Yaung, "Alka-Seltzer Fizzing-Determination of Percent by Mass of NaHCO3 in Alka-Seltzer Tablets," An Undergraduate General Chemistry Experiment, Journal of chemical education, Jul. 2002, 79(7):848.
Domino et al., "Effect of inspired CO2 on ventilation and perfusion heterogeneity in hyperventilated dogs," Journal of Applied Physiology, Sep. 1993, 75(3):1306-14.
Dyer, "Effects of Low and High Oxygen Tensions and Related Respiratory Conditions on Visual Performance: A Literature Review," Chapter 18, Jun. 1988, pp. 199-203.
Fisher et al., Isocapnic hyperpnea accelerates carbon monoxide elimination. American journal of respiratory and critical care medicine, 159(4):1289-92, Apr. 1999.
Grammatopoulou et al., "Hyperventilation in asthma: a validation study of the Nijmegen Questionnaire—NQ," Journal of Asthma, Oct. 2014, 51(8):839-46.
Gronwall, "Paced auditory serial-addition task: a measure of recovery from concussion," Percept. Mot. Skills, 44(2):367-73, Apr. 1977.
Harvey et al., "Effect of carbon dioxide in acute mountain sickness: a rediscovery," The Lancet, Sep. 1988, 332(8612):639-41.
Herma Pharma [online], "Chewable tablets," [retrieved on Sep. 24, 2020], retrieved from: URL<https://www.hermes-pharma.com/dosage-forms-and-drug-delivery/user-friendly-dosage-forms/chewable-tablets/>, 2 pages.
Imray et al., "Birmingham Medical Research Expeditionary Society. Effects of breathing air containing 3% carbon dioxide, 35% oxygen or a mixture of 3% carbon dioxide/35% oxygen on cerebral and peripheral oxygenation at 150 m and 3459 m," Clinical Science, Mar. 2003, 104(3):203-10.
International Preliminary Report on Patentability in International Application No. PCT/US2018/039959 dated Jan. 9, 2020, 10 pages.
International Search Report and Written Opinion in International Application No. PCT/US2018/039959 dated Sep. 11, 2018, 20 pages.
Kregenow and Swenson, "The lung and carbon dioxide: implications for permissive and therapeutic hypercapnia," European Respiratory Journal, Jul. 2002, 20(1):6-11.
McFarland, "Effect of hypoxia on the human," Department of Psychology, Columbia University and the Fatigue Laboratory, Harvard University, pp. 61-66 and 87-89 (with Tables and Bibliography), (1938).
School of Aerospace Medicine, "Effect of Changes in Blood PCO2 on Brain Oxygenation at 147 MM HG Ambient Pressure (39,000 Feet)," Jun. 1962, p. 13.
Stepanek et al., "Acute hypoxic hypoxia and isocapnic hypoxia effects on oculometric features," Aviation, space, and environmental medicine, Jul. 2014, 1;85(7):700-7.
Stepanek et al., "Early detection of hypoxia-induced cognitive impairment using the King-Devick test," Aviation, space, and environmental medicine, Oct. 2013, 84(10):1017-22.
Takeuchi et al., "A simple "new" method to accelerate clearance of carbon monoxide," American journal of respiratory and critical care medicine, 161(6):1816-9, Jun. 2000.

(56) References Cited

OTHER PUBLICATIONS

Van Dorp et al., "Inspired carbon dioxide during hypoxia: effects on task performance and cerebral oxygen saturation," Aviation, space, and environmental medicine, Jul. 2007, 78(7):666-72.
U.S. Appl. No. 16/346,791, filed May 1, 2019, Guarav N. Pradhan, Published.

* cited by examiner

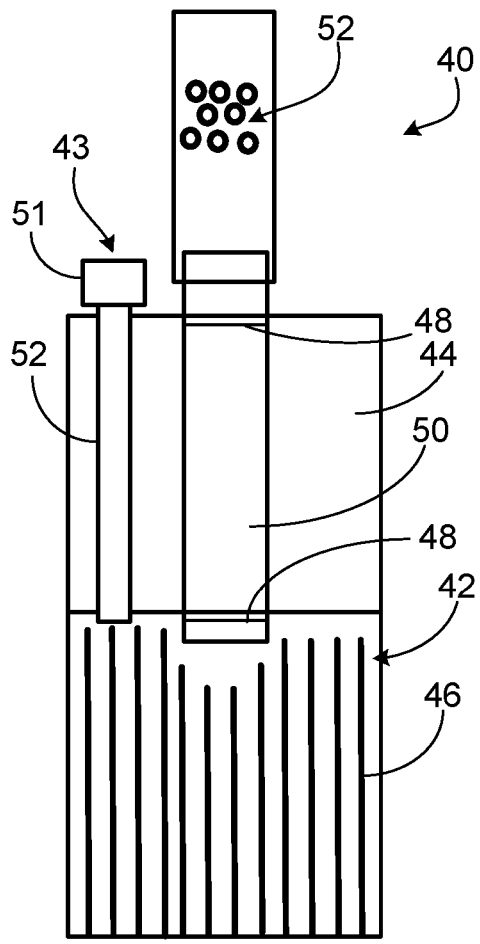
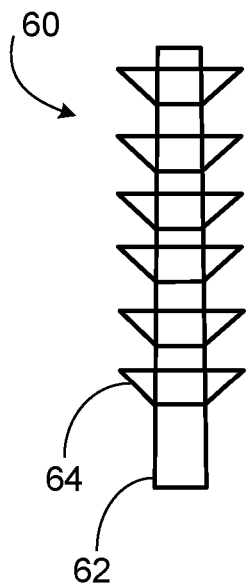
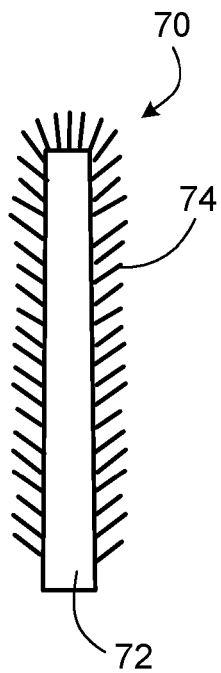
FIG. 4  FIG. 6A  FIG. 6B
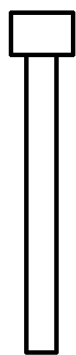
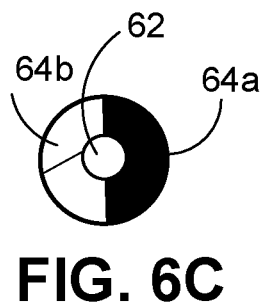
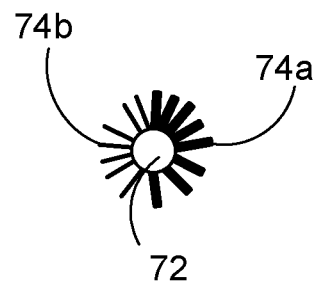
FIG. 5  FIG. 6C  FIG. 6D

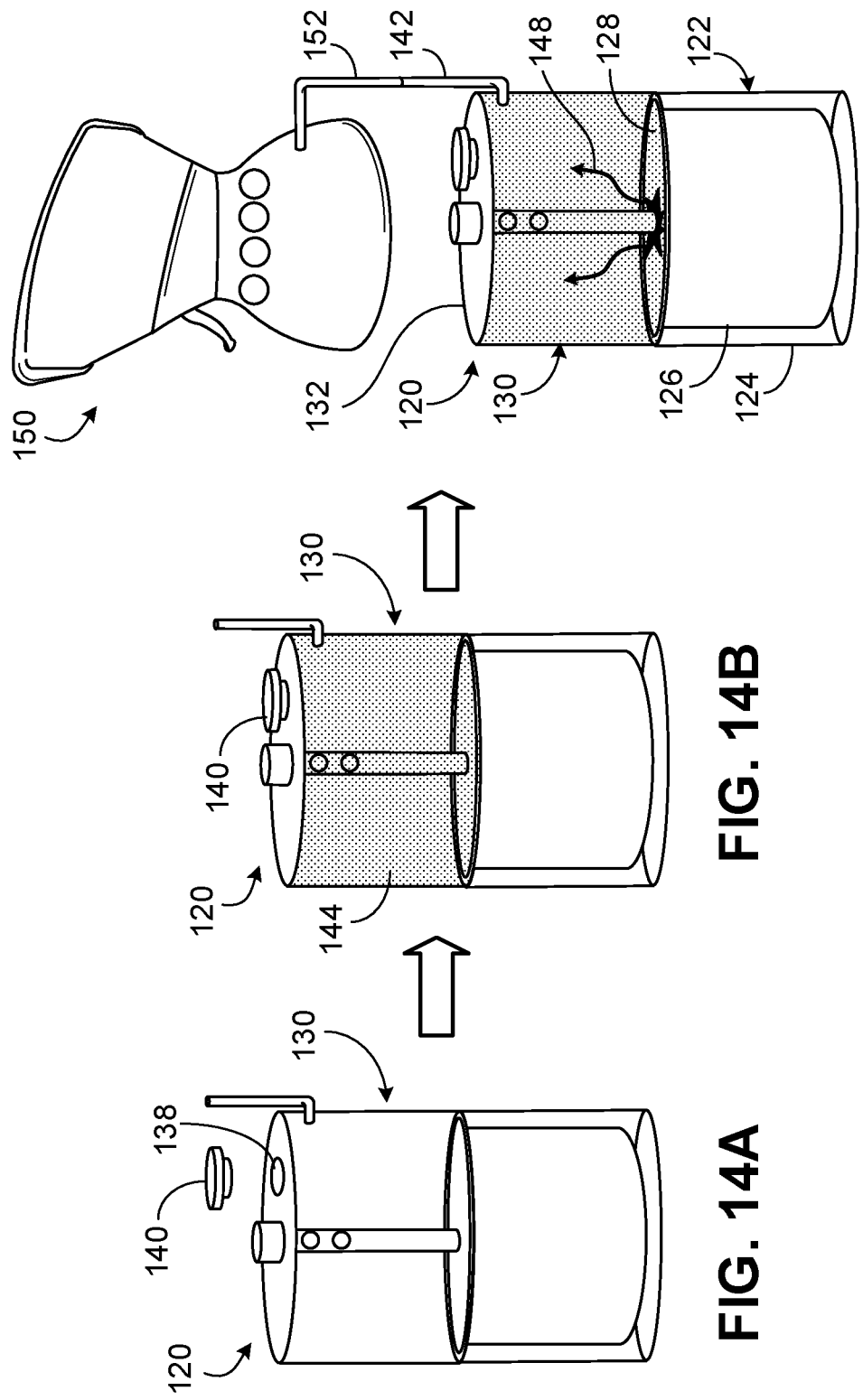

METHODS AND MATERIALS FOR TREATING HYPOCAPNIA

CROSS-REFERENCE TO RELATED APPLICATIONS

This application is a National Stage application under 35 U.S.C. § 371 of International Application No. PCT/US2018/039959, having an International Filing Date of Jun. 28, 2018, which claims priority to U.S. Application Ser. Nos. 62/671,817, filed on May 15, 2018, 62/625,103, filed on Feb. 1, 2018, and 62/526,181, filed Jun. 28, 2017. The disclosure of the prior applications are considered part of the disclosure of this application, and are incorporated in their entirety into this application.

BACKGROUND

1. Technical Field

This document relates to methods and materials involved in treating hypocapnia, a state of decreased carbon dioxide within the body. For example, this document provides methods and materials for delivering carbon dioxide ($CO_2$) to a mammal to treat hypocapnia or compensate for a reduced level of $CO_2$.

2. Background Information

Hypocapnia is a condition where a mammal has a reduced level of carbon dioxide in the blood. It usually occurs as a result of excessive ventilation (e.g., increased depth of breathing and/or increased rate of breathing).

SUMMARY

This document provides methods and materials for treating hypocapnia. For example, this document provides methods and materials for delivering $CO_2$ to a mammal to treat hypocapnia or compensate for a reduced level of $CO_2$. As described herein, delivering $CO_2$ to a mammal suffering from hypocapnia can treat the hypocapnia or compensate for a reduced level of $CO_2$ and rapidly resolve the symptoms of hypocapnia. In some cases, having the ability to reduce hypocapnia and the symptoms of hypocapnia rapidly as described herein can allow a mammal to resume normal activities without needing additional medical care.

In general, one aspect of this document features a composition for placing within the mouth of a mammal, wherein at least 90 percent of the composition comprises an acid and a carbonate, wherein the composition releases $CO_2$ for the mammal to inhale once the composition is placed within the mouth of the mammal or within a cup with liquid from which resulting $CO_2$ gas is inhaled. The mammal can be a human. The acid can be ascorbic acid. The carbonate can be sodium bicarbonate. In some examples, at least 95 percent of the composition can comprise the acid and the carbonate.

In another aspect, this document features a capsule device for delivering $CO_2$ to a mammal. The capsule device comprises, or consists essentially of, a liquid compartment for housing a liquid, a solid compartment for housing a solid, the liquid, the solid, an actuator configured to allow the liquid to contact the solid upon actuation, and a mouthpiece portion, wherein the contact of the liquid with the solid releases $CO_2$ for the mammal to inhale through the mouthpiece. The mammal can be a human. The liquid can be an acid. The acid can be ascorbic acid. The solid can be a carbonate. The carbonate can be sodium bicarbonate.

In another aspect, this document features a mask device for delivering $CO_2$ to a mammal. The mask device comprises, or consists essentially of, a liquid compartment for housing a liquid, a solid compartment for housing a solid, the liquid, the solid, an actuator configured to allow the liquid to contact the solid upon actuation, and a strap to hold the mask device to the face of the mammal, wherein the contact of the liquid with the solid releases $CO_2$ for the mammal to inhale through the mask. The mammal can be a human. The liquid can be an acid. The acid can be ascorbic acid. The solid can be a carbonate. The carbonate can be sodium bicarbonate.

In another aspect, this document features a method for treating a mammal suffering from hypocapnia comprising delivering $CO_2$ to the mammal using a composition, a capsule device, a mask device, a canister device, or a capsule based system in line with an emergency oxygen system (compressed gas, chemical gas generation (oxygen candle), molecular sieve system (oxygen concentrator)). The composition can be for placing within the mouth of a mammal, wherein at least 90 percent of the composition comprises an acid and a carbonate, wherein the composition releases $CO_2$ for the mammal to inhale once the composition is placed within the mouth of the mammal or within a cup with liquid from which resulting $CO_2$ gas is inhaled (e.g., through the mammal's nose, mouth, or both). The mammal can be a human. The acid can be ascorbic acid. The carbonate can be sodium bicarbonate. In some examples, at least 95 percent of the composition can comprise the acid and the carbonate. The capsule device can be for delivering $CO_2$ to a mammal. The capsule device comprises, or consists essentially of, a liquid compartment for housing a liquid, a solid compartment for housing a solid, the liquid, the solid, an actuator configured to allow the liquid to contact the solid upon actuation, and a mouthpiece portion, wherein the contact of the liquid with the solid releases $CO_2$ for the mammal to inhale through the mouthpiece (e.g., through the mammal's nose, mouth, or both). The mammal can be a human. The liquid can be an acid. The acid can be ascorbic acid. The solid can be a carbonate. The carbonate can be sodium bicarbonate. The mask device can be for delivering $CO_2$ to a mammal. The mask device comprises, or consists essentially of, a liquid compartment for housing a liquid, a solid compartment for housing a solid, the liquid, the solid, an actuator configured to allow the liquid to contact the solid upon actuation, and a strap to hold the mask device to the face of the mammal, wherein the contact of the liquid with the solid releases $CO_2$ for the mammal to inhale through the mask. The mammal can be a human. The liquid can be an acid. The acid can be ascorbic acid. The solid can be a carbonate. The carbonate can be sodium bicarbonate.

In another aspect, this document features an oxygen system that include a component for supplying or generating oxygen and a capsule for generating $CO_2$. The component can be a compressed oxygen tank. The component can be a chemical gas generation component. The component can be a molecular sieve system.

In another aspect, this document features a method for treating a mammal suffering from hypocapnia by delivering $CO_2$ to said mammal using the oxygen system.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 4 is a side view of a capsule device for releasing $CO_2$ for inhalation according to some embodiments.

FIG. 5 is a side view of an actuator for use in the capsule device of FIG. 4.

FIGS. 6A and 6B contain side views of solid reactors according to some embodiments.

FIGS. 6C and 6D contain cross sectional views of the solid reactors of FIGS. 6A and 6B, respectively, according to some embodiments.

FIGS. 14A-14C show a method of using the capsule device for releasing $CO_2$ for inhalation of FIG. 10 with the mask of FIG. 13 according to some embodiments.

DETAILED DESCRIPTION

Figure 1:
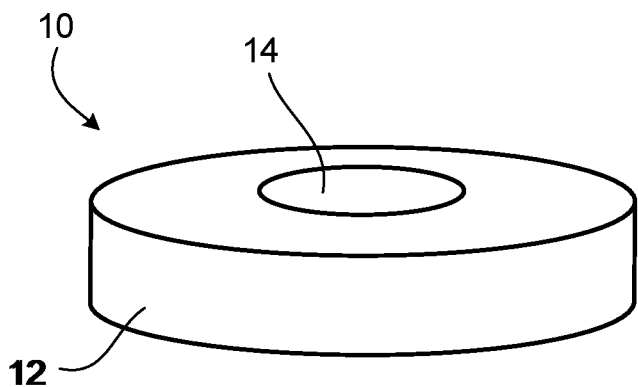
FIG. 1 is a side view of one example of a solid composition formulated to release $CO_2$ for inhalation.

This document provides methods and materials for compensating for or treating hypocapnia. For example, this document provides methods and materials for delivering $CO_2$ to a mammal to treat/compensate for hypocapnia and/or to reduce the symptoms of hypocapnia. Symptoms of hypocapnia that can be reduced (e.g., rapidly reduced) as described herein include, without limitation, dizziness, visual disturbances, anxiety, muscle cramps, tetany, cutaneous signs of paresthesia (e.g., hands, feet, and/or mouth), nausea, headache, difficulty concentrating, imbalance as well as other neurological signs and symptoms, chest tightness, chest pain, bronchoconstriction, and epigastric distress. In some cases, the methods and materials provided herein can be used to treat hyperventilation and/or respiratory alkalosis in a mammal. In some cases, the methods and materials provided herein can have the ability to use $CO_2$ enriched breathing gas as a modality for enhanced treatment of individuals who suffer from carbon monoxide poisoning. In some cases, this can be achieved by enhancing ventilation, carbon monoxide gas washout, and/or tissue oxygen delivery. Using $CO_2$ enriched breathing gas can be more effective as compared to mere oxygen or air inhalation.

Any type of mammal suffering from hypocapnia, hyperventilation, and/or alkalosis can be treated as described herein. For example, humans and other primates such as monkeys having hypocapnia, hyperventilation, and/or alkalosis can be treated with inhaled $CO_2$ (e.g., $CO_2$ supplementation) as described herein. In some cases, dogs, cats, horses, bovine species, pigs, sheep, and rodents can be treated with inhaled $CO_2$ (e.g., $CO_2$ supplementation) as described herein.

Any appropriate method can be used to identify a mammal having hypocapnia, hyperventilation, and/or respiratory alkalosis. For example, clinical signs and symptoms as described above and/or a decrease in $CO_2$ (e.g., measured by end tidal $CO_2$ measurement, arterial, venous, or mixed venous blood gases, and/or direct exhaled gas analysis with capnometry or capnography) can be used to identify a human having hypocapnia. Additional changes that can be seen with acute hypocapnia can include low serum and urine phosphorus, low serum potassium, and/or low serum magnesium. In some cases, a human can self-identify when hypocapnia, hyperventilation, and/or respiratory alkalosis is present based on over breathing and/or being in an environment with reduced air pressure such as a high altitude when mountain climbing or flying. Exposure of a human to high altitude may result in adaptive increases in ventilation, which results in various degrees of hypocapnia. The methods and materials described herein can be used to detect hypocapnia, to correct hypocapnia, and/or to improve performance by adding $CO_2$ to the breathing air of the human.

In some cases, a capnic challenge test provided herein can be used to identify a human having hypocapnia. As described herein, a mammal (e.g., a human) can be assessed, prior to testing, for baseline symptoms and baseline measurements. The baseline symptoms can include, without limitation, items such as chest pain, feeling tense, blurred vision, dizziness, confusion, irregular breathing, shortness of breath, chest tightness, tingling fingers, stiff fingers or arms, tight feeling around mouth, cold hands or feet, palpitations, and/or anxiety feelings. Baseline symptoms can be those recorded on a Nijmegen questionnaire with a score of 23 being positive for disorders associated with decreased carbon dioxide as described elsewhere (Grammatopoulou et al., *J. Asthma*, 51(8):839-846 (2014)). Baseline measurements can include, without limitation, end tidal $CO_2$ recordings, blood pressure (e.g., orthostatic blood pressure), blood oxygen saturation levels, pulse rate, endothelial function, brachial tonometry, spirometry, and galvanic skin resistance. Any appropriate method can be used to measure end tidal $CO_2$. For example, a capnometer (e.g., a Masimo Capnometer) can be used to measure end tidal $CO_2$. Any appropriate method can be used to measure blood oxygen saturation levels and pulse rates. For example, an oximeter (e.g., a Masimo Oximeter) can be used to measure blood oxygen saturation levels and pulse rates.

Once baseline symptoms and baseline measurements are obtained, the $CO_2$ level within the mammal can be reduced over a period of time. For example, the $CO_2$ level within the mammal can be reduced by from about 10 mmHg to about 20 mmHg over a period of time from about 1 minute to about 10 minutes (e.g., from about 1 minute to about 5 minutes, from about 60 seconds to about 180 seconds, or from about 90 to about 120 seconds). For example, the $CO_2$ level within the mammal can be reduced from about 40 mmHg (e.g., 35 mmHg-45 mmHg) to about 20 mmHg (e.g., 15 mmHg-25 mmHg) over a period of time from about 1 minute to about 10 minutes (e.g., from about 1 minute to about 5 minutes, from about 60 seconds to about 180 seconds, or from about 90 to about 120 seconds). Any appropriate method can be used to reduce the $CO_2$ level within a mammal. For example, maximum voluntary ventilation can be used to reduce $CO_2$ levels within a mammal. The inhaled gas can be room air, 100% oxygen, or other oxygen rich mixtures.

In some cases, an increased intensity of ventilation over about 10 to 15 minutes can be used to achieve about 10 mmHg to about 20 mmHg reduction in $CO_2$ levels to demonstrate alterations in cerebral function simulating, for example, high altitude. Such a technique can be used as an educational tool for pilots and mountaineers. In the educational setting, pilots and mountaineers can be trained to learn and recognize the symptoms of hypocapnia. High inhaled oxygen concentration can cause increase in ventilation, which in turn will result in hypocapnia and decreased performance. In one example during training, the inhaled breathing gas mixture can be room air or, in some cases, 100% oxygen. The inhaled gas triggers excess ventilation resulting in hyperoxic hypocapnia, which is especially insidious as the subject perceives to have adequate oxygenation based on the inhaled gas, when the tissue oxygen delivery is markedly impaired by hypocapnic vasoconstriction and a left shift of the oxyhemoglobin dissociation curve.

While in a state of reduced $CO_2$, the mammal (e.g., the human) can be assessed for one or more symptoms and measurements such as any of the symptoms or measurements assessed at baseline. For example, the mammal can be assessed for one or more symptoms such as chest pain, feeling tense, blurred vision, dizziness, confusion, irregular breathing, shortness of breath, chest tightness, tingling fingers, stiff fingers or arms, tight feeling around mouth, cold hands or feet, palpitations, and/or anxiety feelings. Examples of measurements that can be assessed while the mammal is in a state of reduced $CO_2$ can include, without limitation, end tidal $CO_2$ recordings, blood pressure (e.g., orthostatic blood pressure), blood oxygen saturation levels, pulse rate, endothelial function, brachial tonometry, spirometry and skin resistance.

After assessing the mammal for symptoms and/or measurements while the mammal is in a state of reduced $CO_2$, the level of $CO_2$ can be replenished within the mammal. Any appropriate method can be used to restore $CO_2$ levels to their normal levels. For example, the methods and materials provided herein can be used to increase $CO_2$ levels within a mammal. In some cases, oral supplementation of $CO_2$ via an effervescent formulation can be used to increase $CO_2$ levels within a mammal.

As the level of reduced $CO_2$ is being increased, or from about 60 seconds to about 300 seconds after baseline $CO_2$ levels are restored, the mammal (e.g., the human) can be assessed for resolution of one or more symptoms identified during the state of reduced $CO_2$. For example, a mammal that experienced one or more symptoms such as chest pain, feeling tense, blurred vision, dizziness, confusion, irregular breathing, shortness of breath, chest tightness, tingling fingers, stiff fingers or arms, tight feeling around mouth, cold hands or feet, palpitations, and/or anxiety feelings, during the state of reduced $CO_2$ can be assessed to determine if those symptoms resolved upon restoring baseline $CO_2$ levels. In some cases, measurements such as end tidal $CO_2$ recordings, blood pressure (e.g., orthostatic blood pressure), blood oxygen saturation levels, pulse rate, endothelial function, brachial tonometry, spirometry and skin resistance can be assessed as baseline $CO_2$ levels are being restored or after baseline $CO_2$ levels are restored.

Any symptoms that appeared during a state of reduced $CO_2$ and resolved during a return to baseline $CO_2$ levels can be attributed to hypocapnia (e.g., hypocapnia resulting from hyperventilation) and/or acute respiratory alkalosis. In such cases, a mammal (e.g., a human) identified as having hypocapnia and/or respiratory alkalosis via a capnic challenge test provided herein can be treated as described herein. In some cases, a mammal (e.g., a human) identified as having hypocapnia and/or respiratory alkalosis via a capnic challenge test provided herein can be treated, alternatively or additionally, with other therapeutic measures used to optimize breathing.

Once identified as having hypocapnia, hyperventilation, and/or respiratory alkalosis, the mammal can be administered or instructed to self-administer a solid composition formulated to release $CO_2$ for inhalation. In some cases, a solid composition formulated to release $CO_2$ for inhalation can include a mixture of an acid and a carbonate in dry form. Examples of acids that can be used as described herein include, without limitation, acetic acid, tartaric acid, ascorbic acid, malic acid, and citric acid. Examples of carbonates that can be used as described herein include, without limitation, sodium bicarbonate, potassium bicarbonate, and magnesium bicarbonate. As described herein, a solid composition formulated to release $CO_2$ for inhalation can be placed in the mouth of the mammal being treated such that it becomes wet from the mammal's saliva and/or a fluid (e.g., drinking water) the mammal drinks. Once the solid composition formulated to release $CO_2$ for inhalation becomes wet within the mammal's mouth (or in a cup with water), $CO_2$ can be released from the composition (e.g., in a non-exothermic manner) and free to enter the mammal's lungs upon inhalation. In some cases, the mammal can chew the composition to aid in the release of $CO_2$. In some cases, the mammal can inhale through the mouth to aid in delivering the released $CO_2$ to the lungs and exhale through the nose to maintain more $CO_2$ within the mouth region for a subsequent inhalation.

In some cases, a composition formulated to release $CO_2$ for inhalation can be placed inside a container (e.g., a cup or bag). In such cases, introduction of water (or other appropriate liquid such as an acidic liquid) can trigger the release of $CO_2$ for the mammal to inhale from the container.

Any appropriate method can be used to make a solid composition formulated to release $CO_2$ for inhalation. For example, a mixture of ascorbic acid in solid form and sodium bicarbonate in solid form can be compressed into a table. In some cases, ascorbic acid in solid form and sodium bicarbonate in solid form can be layered onto a carrier system to facilitate generation of $CO_2$ gas in cartridges or systems as described herein.

In some cases, a coating can be applied to the composition. In such cases, the coated composition can be chewed to allow the inner materials to contact fluid (e.g., saliva) to release $CO_2$. Examples of materials that can be used as a coating include, without limitation, shellac in combination with polyvinyl pyrrolidone (PVP) to prevent hardening with age, polyvinyl acetate phtalate, and cellulose acetate phtalate, acrylate polymers. In some cases, a sub-coating can be applied to shield an effervescent core from initiation of a reaction once in contact with water. Such a sub-coating can include gelatin, acacia, starch, and/or PVP. In some cases, sugar coatings (e.g., an application of a heated sugar solution 170 degrees with low liquid content using a high pressure spray) can be applied to create a palatable tablet. Information regarding the strength (e.g., amount of expected $CO_2$ released) of the respective tablet based on size can be printed on the tablet surface. See, e.g., U.S. Pat. No. 3,361,631.

In general, a solid composition formulated to release $CO_2$ for inhalation from a tablet (assuming a complete reaction and linear release characteristics over time of dissolution of the solid composition) can include varying amounts of carbonate and acid to release a predetermined amount of $CO_2$ from the solid composition depending on the application and desired amount of $CO_2$ to be released. For example, a solid composition formulated to release $CO_2$ for inhalation from a tablet can include from about 500 mg to about 2000 mg of anhydrous citric acid in solid form and from about 958 mg to about 3,832 mg of sodium bicarbonate in solid form. The chemical reactions and respective $CO_2$ yields can be specific to the type of reactants used, which in turn can depend on the specific application (e.g., oral tablet or capsule system). The use of less hygroscopic acids such as ascorbic acid, fumaric acid, glutaric acid, monosodium citric acid, or disodiumcitric acid can be preferred for the use in environments of higher moisture. The use of more hygroscopic acids, such as citric acid, tartaric acid, and anhydrous citric acid, can be used in sealed applications such as coated tablets or cartridges.

In some cases, a solid composition can be formulated to release about 1 percent, about 3 percent, or about 5 percent $CO_2$ for inhalation assuming normal ventilation rate (e.g., about 15 breaths per minute) and depth (e.g., about 500 mL per breath) and about 100% reaction efficiency. In such cases, the solid compositions can be embossed or printed with an indication of the percentage of $CO_2$ to be provided. For a solid composition designed to release about 1 percent $CO_2$ for inhalation, about 100 mg of anhydrous citric acid in solid form can be formulated with about 191.6 mg of sodium bicarbonate in solid form. For a solid composition designed to release about 3 percent $CO_2$ for inhalation, about 300 mg of anhydrous citric acid in solid form can be formulated with about 574.8 mg of sodium bicarbonate in solid form. For a solid composition designed to release about 5 percent $CO_2$ for inhalation, about 500 mg of anhydrous citric acid in solid form can be formulated with about 958 mg of sodium bicarbonate in solid form.

In some cases, one or more acids and one or more carbonates can be formulated into a pharmaceutically acceptable composition for administration to a mammal. For example, appropriate amounts of acid and carbonate can be formulated together with one or more pharmaceutically acceptable carriers (additives) and/or diluents such that the composition is effective to release $CO_2$ upon contact with a fluid (e.g., saliva). A pharmaceutical composition can be formulated for administration in solid form including, without limitation, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

For applications requiring creation of a solid substrate for a given reaction intended to produce $CO_2$ without a moisture barrier (such as a coating of the reactant combination), a moisture absorbent system containing water absorbing materials (e.g., carboxymethyl cellulose, cellulose ether, polyvinyl pyrrolidon, starch, dextrose (see, e.g., U.S. Pat. No. 4,615,923), gelatin and pectin) can be provided to avoid caking of the formulation, which can reduce the efficient reaction with water.

In some cases, a solid composition formulated to release $CO_2$ for inhalation can include one or more carbonates in dry form with little or no acids in dry form. In such cases, a container containing one or more acids in liquid form can be provided together with the solid composition as a kit. For example, a solid composition containing one or more carbonates in dry form can be packaged together with a container containing one or more acids in liquid form. In some cases, the container can house an acid powder that is rehydrated with, for example, water prior to use.

Figure 2:
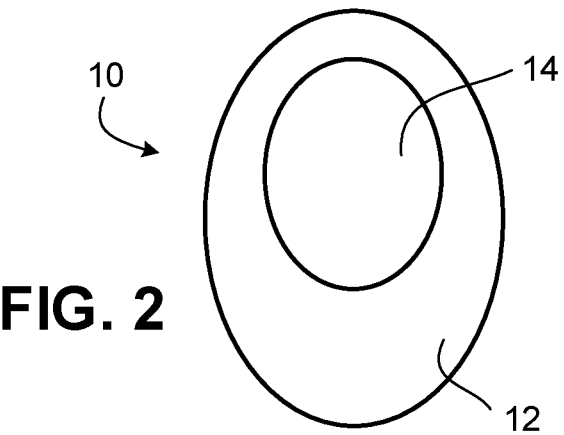
FIG. 2 is a top view of the solid composition of FIG. 1.
Figure 3:
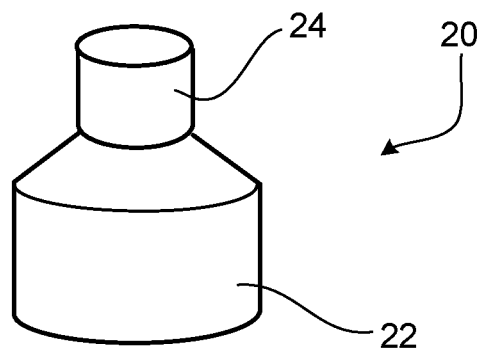
FIG. 3 is a side view of a container for housing a liquid acid according to some embodiments.

With reference to FIGS. 1 and 2, solid composition 10 can contain one or more carbonates in dry form in any appropriate size and any appropriate shape (e.g., oval) for use within a mammal's mouth. Solid composition 10 can have a disc shape 12 and define a hole 14. In some cases, solid composition 10 can have a round shape, an oblong shape, a circular shape, a rectangular shape, an elliptical shape, or other shape for use within a mammal's mouth. In some cases, hole 14 can extend completely through the solid composition 10. In other cases, the solid composition can define a hole that does not extend completely through the composition (e.g., a divot, a recess, or a valley). In some cases, hole 14 can be centered or offset within solid composition 10. In some cases, hole 14 can have a shape corresponding to that of solid composition 10. In some cases, hole 14 can have a shape different than solid composition 10. In some cases, solid composition 10 can include multiple holes 14. Solid composition 10 can be used together with a container 20 or can be packaged within a kit together with a container 20 (FIG. 3). Container 20 can include a lower portion 22 and a lid portion 24 and can house one or more acids in liquid form (e.g., liquid ascorbic acid). In some cases, lid portion 24 can include a narrow opening to control the delivery of the one or more acids. During use, a user can place a solid composition (e.g., solid composition 10) within her mouth and place a few drops of liquid acid onto the solid composition or within a hole (e.g., hole 14) of the solid composition. The hole can help retain the liquid acid in contact with the carbonate material of the composition. The addition of acid to the composition containing one or more carbonates can result in the release of $CO_2$ for the user to inhale.

In some cases, a solid composition provided herein can include nut butter to help adhere the composition to the roof of a user's mouth.

In some cases, a composition formulated to release $CO_2$ for inhalation as described herein can be incorporated into a food or candy product. For example, a coated tablet of various sizes, a nutritional bar, candy, or chewing gum can be designed to include the components needed to release $CO_2$ for inhalation as described herein.

In some cases, an article of manufacture (e.g., a capsule device) can be designed to contain one or more acids in liquid form and one or more carbonates in solid form. In some cases, the acid(s) can be maintained within the article of manufacture in a manner that prevents the acids from contacting the carbonate(s) until ready for use. In such cases, the user can activate the article of manufacture by manipulating it such that the acid(s) come in contact with the carbonate(s), thereby releasing $CO_2$ for the user to inhale. For example, the user can activate the article of manufacture by breaking, bending, chewing, or otherwise breaking a seal in the article of manufacture.

With reference to FIG. 4, capsule device 40 can include a solid compartment 42 and a liquid compartment 44. Solid compartment 42 can house one or more solid reactors 46 that include a material used to generate $CO_2$. For example, solid reactors 46 can include one or more carbonates in solid form. As shown in FIGS. 6A and 6C, solid reactors 46 can be configured in any appropriate shape. For example, solid reactors 46 can be configured in a stacked disc arrangement 60. The stacked disc arrangement 60 can include a shaft portion 62 and multiple disc portions 64. In some cases, shaft portion 62 and/or disc portions 64 can be made of material used to generate $CO_2$ (e.g., one or more carbonates). In some cases, shaft portion 62 and disc portions 64 can be made of material that does not generate $CO_2$. In such cases, shaft portion 62 and/or disc portions 64 can be coated with material used to generate $CO_2$ (e.g., one or more carbonates). For example, disc portion 64 can be coated with material used to generate $CO_2$ (e.g., one or more carbonates) as shown in FIG. 6C as disc portion 64a, compared to disc portion 64b. In some cases, a part of disc portion 64 can be coated (64a) and part can be uncoated (64b). In some cases, the entire disc portion 64 can be coated.

As also shown in FIGS. 6B and 6D, solid reactors 46 can be configured in a spiked arrangement 70. The spiked arrangement 70 can include a shaft portion 72 and multiple spike portions 74. In some cases, shaft portion 72 and/or spike portions 74 can be made of material used to generate $CO_2$ (e.g., one or more carbonates). In some cases, shaft portion 72 and spike portions 74 can be made of material that does not generate $CO_2$. In such cases, shaft portion 72 and/or spike portions 74 can be coated with material used to generate $CO_2$ (e.g., one or more carbonates). For example, spike portion 74 can be coated with material used to generate $CO_2$ (e.g., one or more carbonates) as shown in FIG. 6D as spike portion 74a, compared to spike portion 74b. In some cases, a part of spike portion 74 can be coated (74a) and part can be uncoated (74b). In some cases, the entire spike portion 74 can be coated.

Referring back to FIG. 4, liquid compartment 44 can house one or more liquids that generate $CO_2$ when they contact solid reactors 46. For example, liquid compartment 44 can house one or more liquid acids (e.g., acetic acid, tartaric acid, ascorbic acid, citric acid, and/or malic acid) that can generate $CO_2$ when they contact solid reactors 46 (e.g., solid reactors containing one or more carbonates).

Capsule device 40 can include an actuator mechanism 43 that allows a user to activate the device such that liquid housed within liquid compartment 44 can enter solid compartment 42. Actuator mechanism 43 can include an actuator 51 (FIG. 5) located within a channel 52. Pressing actuator 51 can create an opening between liquid compartment 44 and solid compartment 42. In some cases, pulling back on actuator 51 can increase the speed at which liquid from liquid compartment 44 can enter solid compartment 42.

Capsule device 40 can include a $CO_2$ line 50 that allows $CO_2$ to exit solid compartment 42. $CO_2$ line 50 can include one or more filters 48. Filter(s) 48 can have any appropriate pore size (e.g., from about 0.5 µm to about 50 µm). In some cases, filter(s) 48 can be designed to prevent solids and liquid reaction components from being inhaled by a user. In some cases, capsule device 40 can include a mouthpiece portion 52 attached to $CO_2$ line 50. Mouthpiece portion 52 can include a plurality of openings to allow $CO_2$ to exit the mouthpiece portion 52 and enter a user's mouth during use.

During use, once liquid from liquid compartment 44 enters solid compartment 42 and contacts solid reactors 46, $CO_2$ can be released. The released $CO_2$ can exit solid compartment 42 via $CO_2$ line 50 and pass though one or more filters 48 as it travels from $CO_2$ line 50 to mouthpiece portion 52. Once within mouthpiece portion 52, the $CO_2$ can exit mouthpiece portion 52 via openings and enter the user's mouth.

In some cases, a mask device can be designed to contain one or more acids in liquid form and one or more carbonates in solid form. In some cases, the acid(s) can be maintained within the mask device in a manner that prevents the acids from contacting the carbonate(s) until ready for use or in line with an emergency or regular aircraft oxygen system, such as in aircraft or other low oxygen environments (mountaineering, unpressurized aircraft, or depressurization of an aircraft pressure cabin). In such cases, the user can activate the mask device by manipulating it with an emergency actuation such that the acid(s) come in contact with the carbonate(s), thereby releasing $CO_2$ for the user to inhale.

In some cases, an oxygen system (e.g., an aircraft oxygen system) that can be configured to include a device for generating $CO_2$ as described herein (e.g., a composition containing one or more acids and one or more carbonates) can be a compressed oxygen gas system, a chemical oxygen generation system, and/or a molecular sieve oxygen system. For example, a compressed oxygen gas system can include compressed oxygen. As another example, a chemical oxygen generation system can include an oxygen candle. In some cases, an oxygen candle contains a mix of sodium chlorate and iron powder, which when ignited produces sodium chloride, iron oxide, and at a fixed rate about 6.5 man-hours of oxygen per kilogram of the mixture. A molecular sieve oxygen system can use atmospheric air and/or bleed air (air produced by an engine) and can concentrate all the gases present except oxygen and argon, which can then be provided as an oxygen enriched breathing gas.

Figure 7:
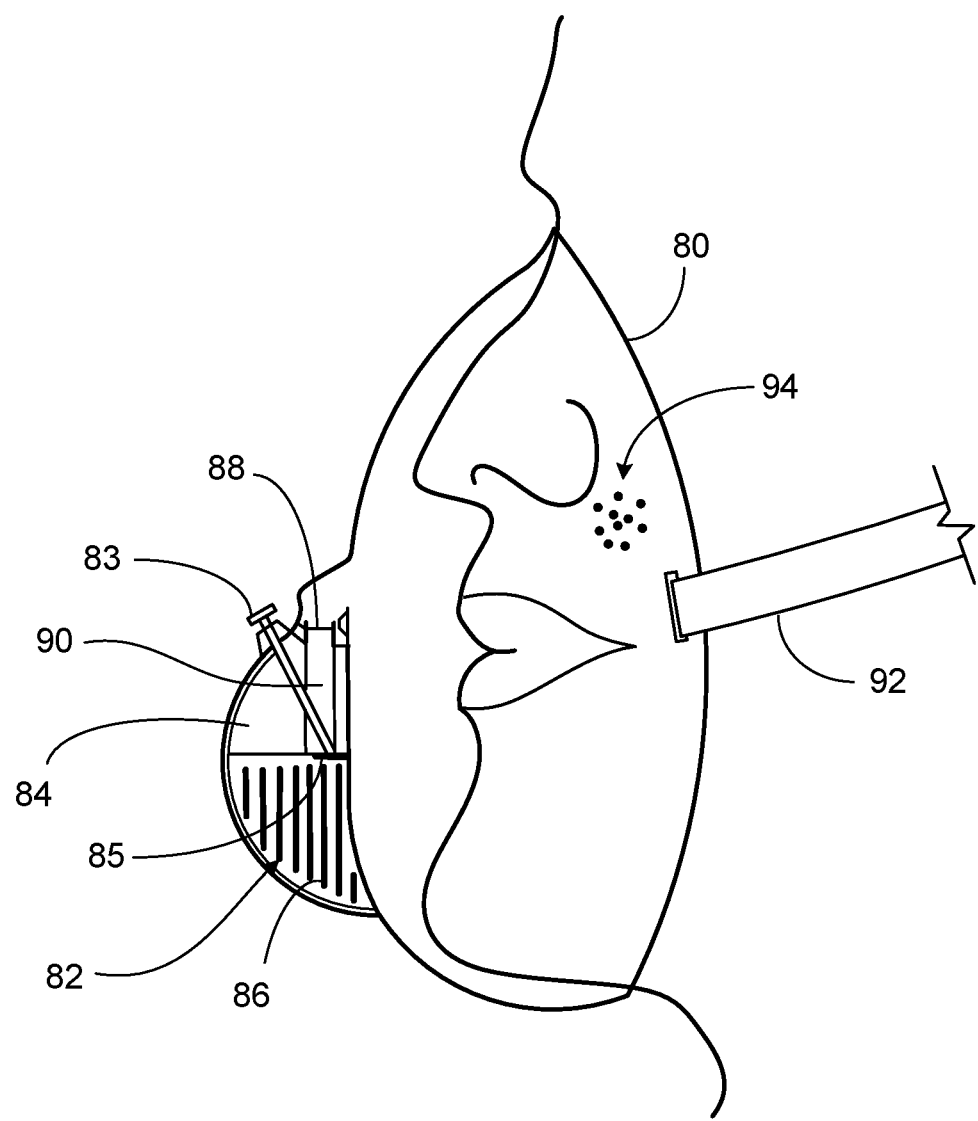
FIG. 7 is a side view of a mask device for releasing $CO_2$ for inhalation according to some embodiments.

With reference to FIG. 7, mask device 80 can include a solid compartment 82 and a liquid compartment 84. Solid compartment 82 can house one or more solid reactors 86 that include a material used to generate $CO_2$. For example, solid reactors 86 can include one or more carbonates in solid form. Solid reactors 86 can be configured in any appropriate shape or configuration such as those described herein for solid reactors 46 (FIG. 6).

Liquid compartment 84 can house one or more liquids that generate $CO_2$ when they contact solid reactors 86. For example, liquid compartment 84 can house one or more liquid acids (e.g., acetic acid, tartaric acid, ascorbic acid, citric acid, and/or malic acid) that can generate $CO_2$ when they contact solid reactors 86 (e.g., solid reactors containing one or more carbonates).

Mask device 80 can include an actuator mechanism 83 that allows a user to activate the device such that liquid housed within liquid compartment 84 can enter solid compartment 82. Actuator mechanism 83 can include an actuator located within a channel. Pressing the actuator can create an opening between liquid compartment 84 and solid compartment 82 at seal 85. In some cases, pulling back on the actuator can increase the speed at which liquid from liquid compartment 84 can enter solid compartment 82.

Mask device 80 can include a $CO_2$ line 90 that allows $CO_2$ to exit solid compartment 82. $CO_2$ line 90 can include one or more filters 88. Filter(s) 88 can have any appropriate pore size (e.g., from about 0.5 µm to about 50 m). In some cases, filter(s) 88 can be designed to prevent acidic reaction components and solids from being inhaled by a user. In some cases, mask device 80 can include a strap 92 (e.g., an elastic strap) and can define a plurality of openings 94. Openings 94 can allow ambient air to enter the mask device for the user to inhale.

During use, once liquid from liquid compartment 84 enters solid compartment 82 and contacts solid reactors 86, $CO_2$ can be released. The released $CO_2$ can exit solid compartment 82 via $CO_2$ line 90 and pass though one or more filters 88 as it travels from $CO_2$ line 90 to the inner portion of the mask device for the user to inhale through the user's nose, mouth, or both.

Figure 8:
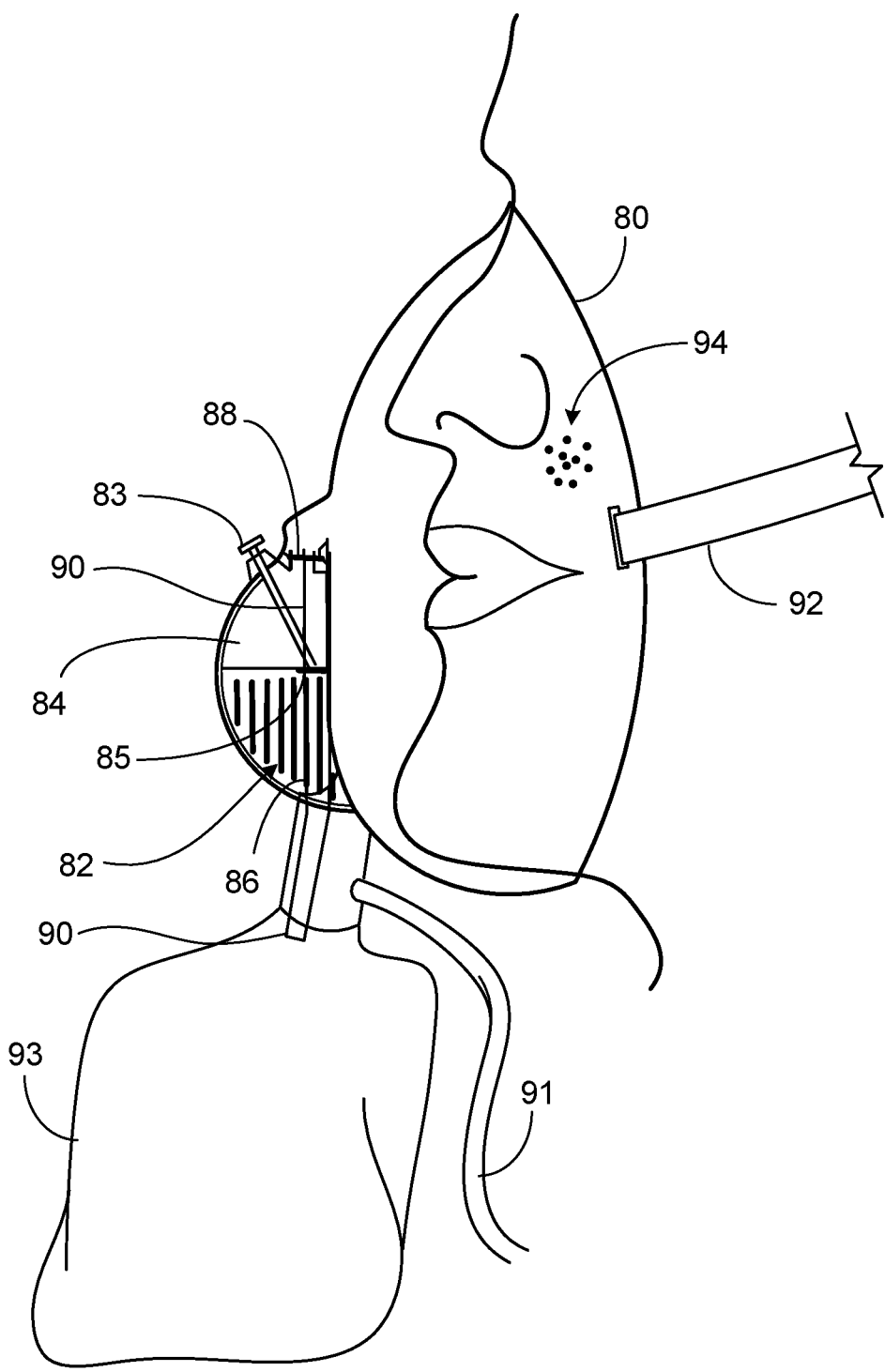
FIG. 8 is a side view of a mask device for releasing $CO_2$ for inhalation according to some embodiments.

In some cases, a mask device provided herein can include a rebreather. As shown in FIG. 8, mask device 80 can include a rebreather bag 93. The rebreather bag may have a volume from about 0.5 L to about 1 L. The rebreather bag can allow retention of $CO_2$ gas for an extended time period beyond the reaction time of the solid reactor. In some cases, mask device 80 can include an oxygen line 91 for providing $O_2$ to the user for inhalation.

In some cases, a capsule device or a mask device provided herein can include a $CO_2$ gas supply component and an oxygen supply component. The $CO_2$ gas supply component and the oxygen supply component can be included in a single container or in separate containers. In one embodiment, a capsule device or a mask device can be configured to couple with a compressed oxygen enriched gas source (e.g., a canister) and can provide simultaneous enrichment of breathing gas with both $O_2$ and $CO_2$.

Figure 9:
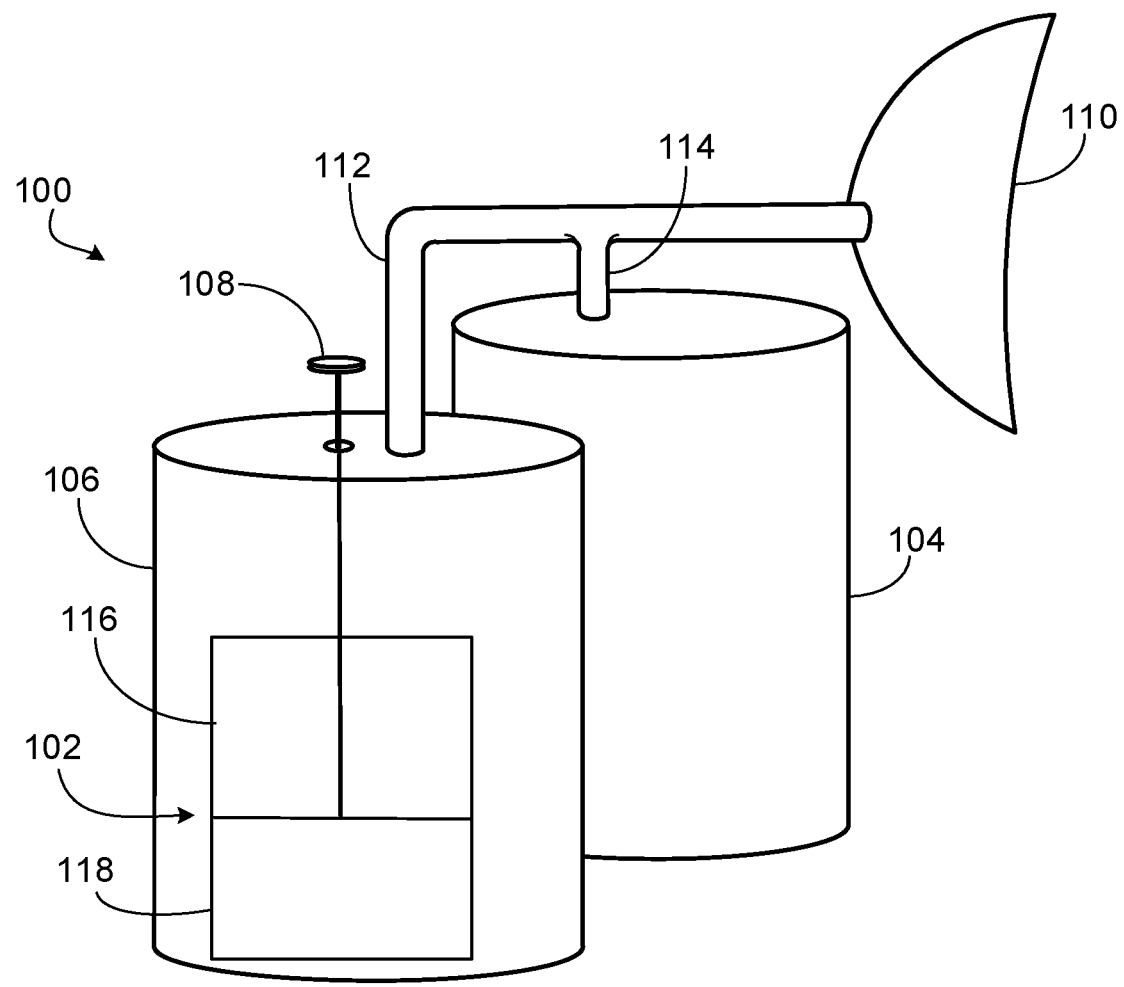
FIG. 9 is a side view of a mask device for releasing $CO_2$ for inhalation according to some embodiments.

With reference to FIG. 9, a mask device 100 provided herein can include a $CO_2$ canister 106 coupled to an oxygen canister 104 (e.g., 95% oxygen). A $CO_2$ capsule device 102 can be encased within $CO_2$ canister 106. $CO_2$ capsule device 106 can include an actuator 108. A user can trigger the generation of $CO_2$ gas by actuating the capsule device to initiate mixing of liquid (e.g., a liquid that generates $CO_2$) and solid reactant (e.g., one or more solid reactors). A mouthpiece portion 110 can be in communication with both a $CO_2$ line 112 from the $CO_2$ canister 106 and an oxygen line 114 from the oxygen canister 104 for providing both $O_2$ and $CO_2$ to the user for inhalation (e.g., through the user's nose, mouth, or both).

In some cases, a canister device 100 provided herein can include an oxygen module 104, a $CO_2$ module 102 inside a $CO_2$ canister 106, a mouthpiece 110, and an actuator 108. The $CO_2$ module 102 can include a liquid compartment 116 for housing a liquid (e.g., an acid) and a solid compartment 118 for housing a solid (e.g., a carbonate). An actuator 108 can be configured to allow the liquid to contact the solid upon actuation to release $CO_2$. The oxygen module 104 can include at least one oxygen gas source (e.g., pressurized oxygen gas, molecular sieve derived oxygen, or liquid oxygen). The mouthpiece 110 can be in fluid communication with a $CO_2$ line 112 connected to the $CO_2$ module 106 and an oxygen line 114 connected to the oxygen module 104.

In one example, a canister device provided herein can include one actuator with a coupled mechanism to trigger simultaneous release of $CO_2$ from the $CO_2$ module and oxygen gas supply from an oxygen module for delivery of $CO_2$/oxygen breathing gas mixture through the mouthpiece.

In some cases, a canister device provided herein can include two actuators (e.g., one $CO_2$ actuator and one oxygen actuator). The $CO_2$ actuator can be configured to trigger a $CO_2$ supply from $CO_2$ module via the contacting of an acidic fluid and carbonate solid. The oxygen actuator can be configured to trigger oxygen delivery from an oxygen module. In some cases, the two actuators can be separately actuated. In some cases, a two-actuator canister device can deliver only $CO_2$ or only oxygen when only one actuator is actuated without actuation of the other. In some cases, both actuators can be actuated simultaneously or in succession to deliver a mixture of $CO_2$ and oxygen gas.

Figure 10:
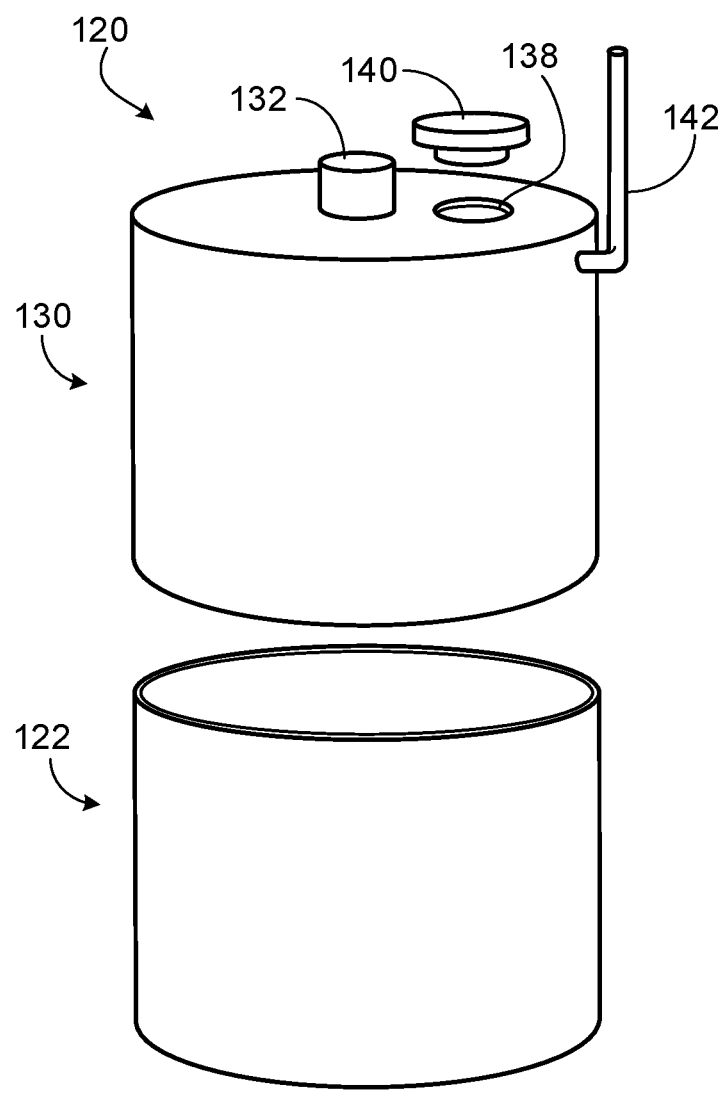
FIG. 10 is a perspective partially exploded view of a capsule device for releasing $CO_2$ for inhalation according to some embodiments.
Figures 11A, 11B:
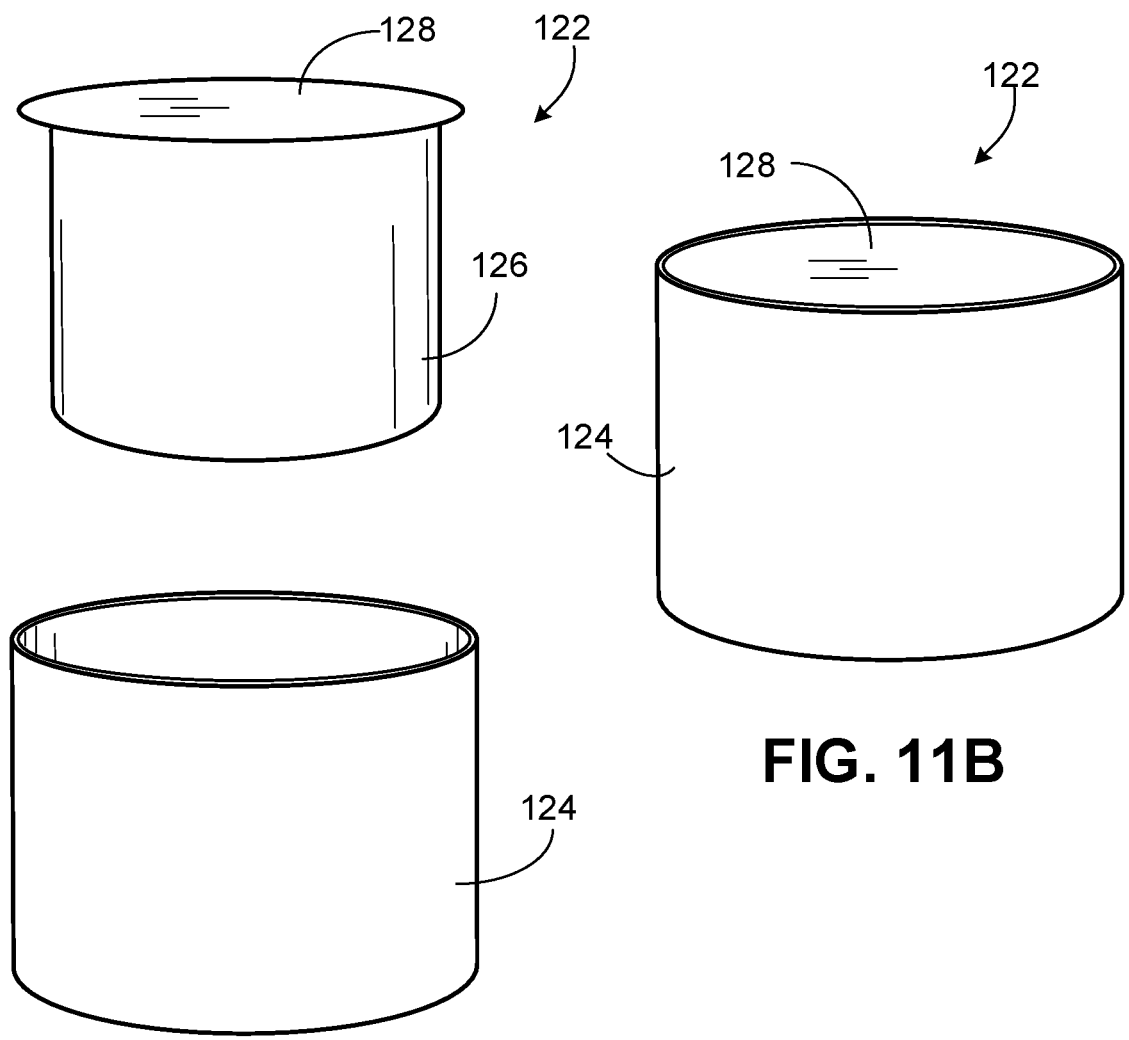
FIG. 11A is a perspective exploded view of a lower vessel of the capsule device for releasing $CO_2$ for inhalation of FIG. 10 according to some embodiments.
FIG. 11B is a perspective view of the lower vessel of FIG. 11A according to some embodiments.
Figure 12:
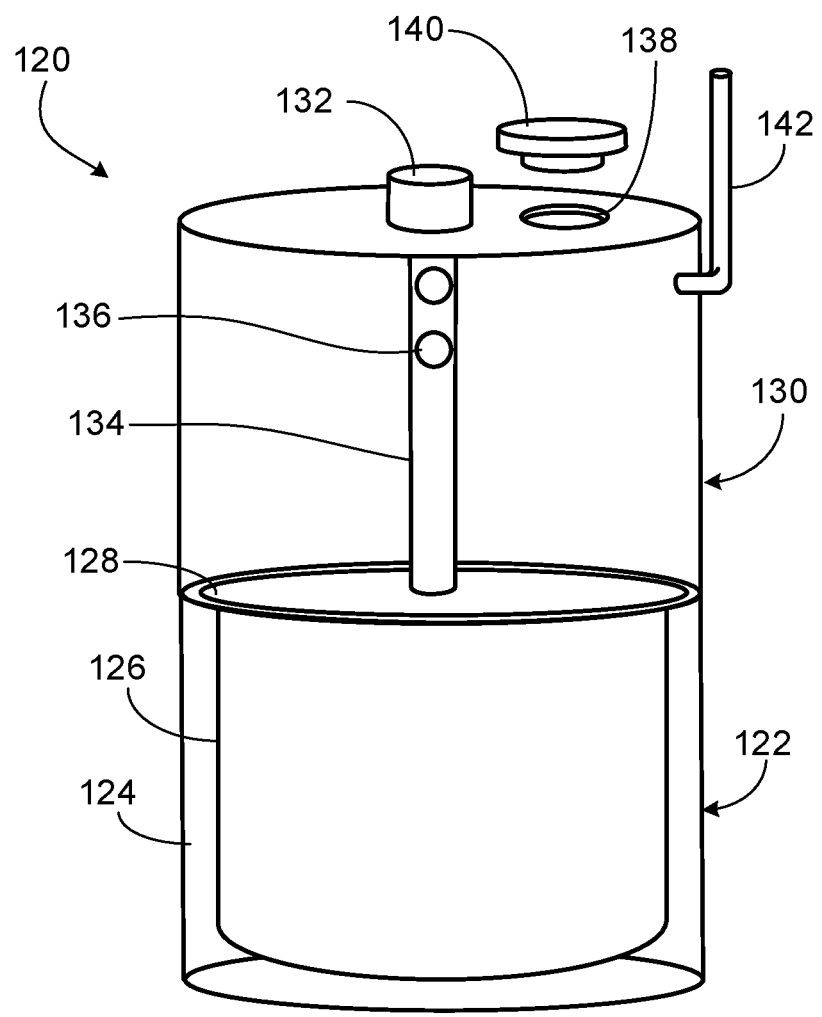
FIG. 12 is a perspective view of the capsule device for releasing $CO_2$ for inhalation according to some embodiments.

Referring to FIGS. 10-12, a capsule device 120 for releasing $CO_2$ for inhalation provided herein can include a lower vessel 122 and an upper vessel 130. In some cases, lower vessel 122 can be removably coupled to upper vessel 130, such that different lower vessels 122 can be attached to upper vessel 130. For example, lower vessel 122 and upper vessel 130 can have a snap fit, can screw together, or other type of fit locking and sealing lower vessel 122 and upper vessel 130. Therefore, a user may be able to use the capsule device 120 multiple times with different lower vessels 122. Alternatively, or in addition, components of lower vessel 122 can be changed to use lower vessel 122 multiple times, as described below. In some cases, lower vessel 122 can house a solid reactor (e.g., one or more carbonates in solid form). In some cases, upper vessel 130 can house a liquid (e.g., acetic acid, tartaric acid, ascorbic acid, citric acid, and/or malic acid). In some cases, upper vessel 130 can receive a liquid. In some cases, upper vessel 130 can house an acid powder that is rehydrated with, for example, water prior to use.

As shown in FIGS. 11A and 11B, lower vessel 122 can include a container 124, a solid reactor capsule 126, and a seal 128. In some cases, solid reactor capsule 126 and seal 128 can be coupled to one another such that a solid reactor capsule 126 can be placed inside a container 124 of lower vessel 122. In some cases, seal 128 can extend beyond an edge of solid reactor capsule 126 to cover an opening of container 124 when solid reactor capsule 126 is placed inside container 124. In some cases, seal 128 extends beyond an inner diameter of container 124 to hold solid reactor capsule 126 in container 124 such that a bottom of solid reactor capsule 126 does not rest on a bottom of container 124. In some cases, container 124 can include a ridge to receive a portion of solid reactor capsule 124 (e.g., seal 128) such that a bottom of solid reactor capsule 126 does not rest on a bottom of container 124. Solid reactor capsule 126 can include a solid reactor. For example, the solid reactor can include one or more carbonates in solid form. In some cases, solid reactor capsule 126 can include an acid powder that is rehydrated with, for example, water prior to use. In some cases, solid reactor capsule 126 can include both the carbonate and the acid, such that when water is added a $CO_2$ reaction occurs.

Referring to FIGS. 10 and 12, upper vessel 130 defines a reservoir and can include an actuator 132, an aperture 138, a cover 140, and a $CO_2$ gas line 142.

Actuator 132 allows a user to activate the capsule device 120 such that liquid housed or received within upper vessel 130 can enter lower vessel 122. In some cases, actuator 132 can include an actuator located within a channel (e.g., a channel 134). In some cases, channel 134 can include one or more holes 136 to allow fluid to enter channel 134. In other cases, an elongated portion 134 of actuator 132 can include one or more holes 136, such that fluid can enter elongated portion 134. In some cases, by allowing fluid to enter holes 136, fluid can enter lower vessel 122 more rapidly when seal 128 is broken by activation of actuator 132. Pressing actuator 132 can create an opening between upper vessel 130 and lower vessel 122. In some cases, pulling back on actuator 132 can increase the speed at which liquid from upper vessel 130 can enter lower vessel 122.

Aperture 138 can allow fluid (e.g., water) to enter into upper vessel 130. Aperture 138 can receive cover 140. In some cases, a seal is created between aperture 138 and cover 140. In some cases, cover 140 and aperture 138 couple together (e.g., via a snap fit, a threaded coupling, a push fit seal).

$CO_2$ gas line 142 can extend from upper vessel 130 towards a mask 150 (shown in FIG. 13) to provide fluid coupling of upper vessel 130 to mask 150 to provide $CO_2$ for inhalation to a user. In some cases, $CO_2$ gas line 142 is rigid. In other cases, $CO_2$ gas line 142 is flexible.

Figure 13:
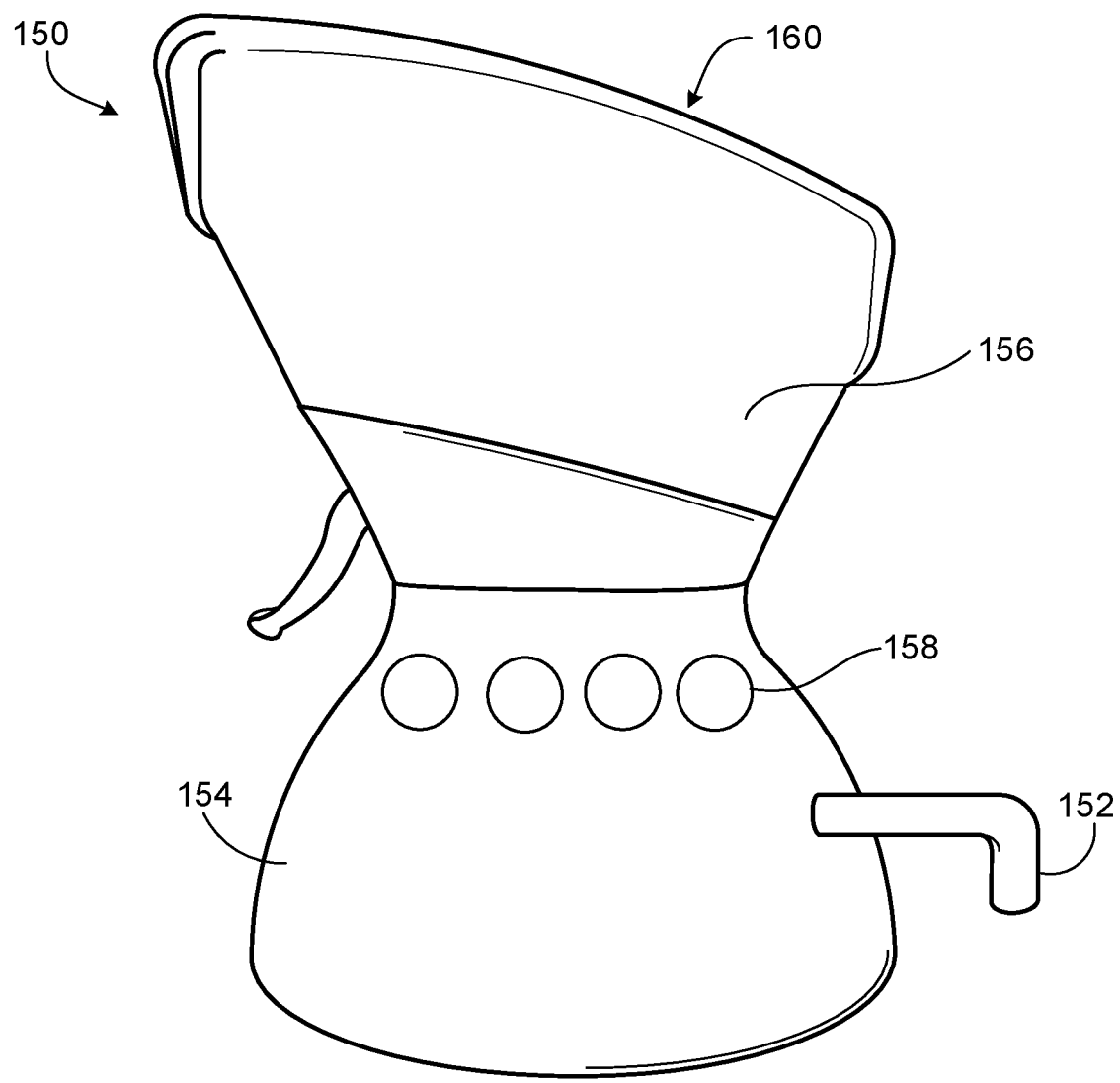
FIG. 13 shows a perspective view of a mask for use with the capsule device for releasing $CO_2$ for inhalation of FIG. 10 according to some embodiments.

Referring to FIG. 13, a mask 150 for use with the capsule device 120 for releasing $CO_2$ for inhalation can include a $CO_2$ gas line 152, a lower chamber 154, and an upper chamber 156. $CO_2$ gas line 152 can feed $CO_2$ from capsule device 120 (e.g., via $CO_2$ gas line 142) into lower chamber 154. In some cases, $CO_2$ gas line 152 and $CO_2$ gas line 142 can be removably coupled (e.g., via a snap fit, a threaded coupling mechanism, or other coupling technique) together. In some cases, $CO_2$ gas line 152 and $CO_2$ gas line 142 are permanently coupled together. In some cases, $CO_2$ gas line 152 is rigid. In other cases, $CO_2$ gas line 152 is flexible.

Lower chamber 154 can capture $CO_2$ from $CO_2$ gas line 152 to provide $CO_2$ to a user for inhalation. In some cases, lower chamber 154 can define one or more apertures 158. Apertures 158 can allow air from the atmosphere, and specifically oxygen, to enter lower chamber 154 and mix with the $CO_2$ gas. In some cases, apertures 158 can be located closer to upper chamber 156 than $CO_2$ gas line 152. In some cases, a plurality of apertures 158 can surround lower chamber 154.

Upper chamber 156 can be fluidly coupled to lower chamber 154. In some cases, upper chamber 156 can have an opening 160 configured for placement over a nose and/or a mouth of a user. In some cases, a fluid opening between upper chamber 156 and lower chamber 154 can have a diameter smaller than a diameter of the opening 160 for placement on the user. In some cases, opening 160 can be shaped to provide a seal between upper chamber 156 and a face of the user.

In some cases, a portion of mask 150 can include a handle, ridges, bumps, or other means of aiding a user in holding mask 150. In some cases, mask 150 can include a strap configured to extend around a head of the user. In some cases, the strap can be adjustable. In some cases, mask 150 can be connected with an oxygen supply source.

Referring to FIGS. 14A-14C, a method of using the capsule device 120 for releasing $CO_2$ for inhalation with the mask 150 can include opening cover 140, adding liquid 144 (e.g., water) through aperture 138 into upper vessel 130, replacing cover 140, connecting (e.g., via a snap engagement) $CO_2$ gas line 142 of capsule device 120 to $CO_2$ gas line 152 of mask 150, and pressing actuator 132, causing seal 128 to break. Breaking seal 128 can cause water to enter lower vessel 122 and cause a reaction with solid reactor capsule 126 such that $CO_2$ 148 is released. $CO_2$ 148 can travel through upper vessel 130, $CO_2$ gas lines 142 and 152 to mask 150, such that $CO_2$ can be inhaled by the user.

In some cases, a mixture of $CO_2$ and oxygen gas can be designed to deliver a particular concentration to of $CO_2$, a particular concentration of oxygen, or particular concentrations of both $CO_2$ and oxygen. In some cases, those $CO_2$ and/or oxygen concentrations can be predetermined based on use at a particular altitude. In some cases, the concentration of $CO_2$ and/or oxygen can be determined using a calculation of $CO_2$ in percent inhaled to achieve a sea level normal $CO_2$ (assuming 40 mmHg) as described elsewhere (see, e.g., Chapter 10 by Clayton White in Handbook of respiratory physiology: Respiratory physiology in aviation 1954, Walter M. Boothby, US Air Force School of Aviation Medicine, Randolph Field, especially the calculations and data from FIG. 2, FIG. 4, and Table 1).

In some cases, a device designed to generate $CO_2$ gas as described herein (e.g., a $CO_2$ module described herein) can be incorporated into an existing oxygen supply system such as an oxygen supply system of an aircraft. For example, a capsule system as described herein can be placed in line with an oxygen source (e.g., molecular sieve oxygen system, emergency oxygen system, bail out bottle, or oxygen generator) to provide $CO_2$ in addition to the emergency oxygen provided. For example, an oxygen system can include a compressed oxygen gas system, a chemical oxygen generation system, and/or a molecular sieve oxygen system.

In some cases, an oxygen system (e.g., an aircraft oxygen system) that can be configured to include a device for generating $CO_2$ as described herein (e.g., a composition containing one or more acids and one or more carbonates) can be a compressed oxygen gas system, a chemical oxygen generation system, and/or a molecular sieve oxygen system. For example, a compressed oxygen gas system can include compressed oxygen. As another example, a chemical oxygen generation system can include an oxygen candle. In some cases, an oxygen candle contains a mix of sodium chlorate and iron powder, which when ignited produces sodium chloride, iron oxide, and at a fixed rate about 6.5 man-hours of oxygen per kilogram of the mixture. A molecular sieve oxygen system can use atmospheric air and/or bleed air (air produced by an engine) and can concentrate all the gases present except oxygen and argon, which can then be provided as an oxygen enriched breathing gas.

The compositions, articles of manufacture, and mask devices provided herein can be used to treat hypocapnia, to compensate for low levels of $CO_2$, to treat carbon monoxide intoxication, to enhance oxygenation, and/or to enhance performance and safety at high altitudes (e.g., at altitudes greater than 1500 m). The inhaled $CO_2$ provided as described herein can right shift oxygen-Hb dissociation curves, increase cerebral perfusion, enhance tissue oxygen delivery, increase cerebral tissue oxygen reserve time, enhance cognitive performance, enable dislodging of carbon monoxide (CO) from hemoglobin molecules, and/or mitigate deleterious hypocapnia. In some cases, the compositions, articles of manufacture, and mask devices provided herein can be used to supply $CO_2$ for treatment of CO poisoning with oxygen, to enhance altitude hypoxia resistance (oxygen sparing), to provide emergency depressurization of aircraft, to provide a differential diagnosis of hypoxia vs. hypocapnia at altitude, and/or to provide field use to increase tissue oxygenation.

The invention will be further described in the following examples, which do not limit the scope of the invention described in the claims.

Example 1—Capnic Challenge Test

In one embodiment, a capnic challenge test is performed as described in this example.
Supplies/Equipment
 Masimo Capnometer
 Masimo Oximeter Blood pressure monitor
Masimo Emma Airway Adapter (disposable)
Hudson RCI Universal Cuff Adapter (disposable)
Airlife Nose Clip (disposable)
Mouthpiece (disposable)
Timer or watch
Paper forms: Nijmegen Questionnaire and Capnic Challenge Test form
Preparation for Testing
1. Ensure patient obtained effervescent tablets from pharmacy prior to beginning test
2. Have patient fill out Nijmegen Questionnaire
3. Procedure is explained to patient
a. Individual is seated in a quiet standard room
b. Demonstrate correct breathing pattern for test
c. Instruct the patient to raise their hand at any time during the testing if he/she experiences symptoms or discomfort and wishes to stop the test
4. Assemble mouthpiece using aseptic technique
5. Connect Masimo Capnometer to mouthpiece and turn it on
6. Place one effervescent tablet on a paper towel with a cup of water next to where patient is seated
Testing the Patient
1. Pulse oximeter is attached, and baseline oxygen saturation is obtained and recorded on Capnic Challenge Form (leave continuous pulse oximeter on)
2. Blood pressure cuff is attached/obtain baseline blood pressure—record on Capnic Challenge Form (Leave BP cuff on)
3. Obtain baseline End Tidal $CO_2$ reading (ask patient to breath normally into mouthpiece) and record reading on Capnic Challenge Form
4. Ask the patient to breathe fast and deep for 90 seconds up to 2 minutes
5. The test can be ended at any time for patient subjective discomfort or clinical reasons
6. At the end of the timed 2 minutes:
a. Obtain End Tidal $CO_2$ level, oxygen saturation, blood pressure, and heart rate, and document on Capnic Challenge Form
b. Provide the patient half of an effervescent tablet and instruct them to hold it on their tongue (or chew it) while breathing through their mouth and out their nose a few times
c. Patient may be allowed to drink some water if mouth is dry from rapid breathing
7. Allow the patient to check symptoms on the Nijmegen sheet that he/she experienced during the rapid breathing portion of the test
8. If the above symptoms have dissipated:
a. Obtain a final End Tidal $CO_2$ level, oxygen saturation, blood pressure, and heart rate, and document on the Capnic Challenge Form
9. If End Tidal $CO_2$ is not returned to the baseline level noted at the beginning of the test, then the second half of the effervescent tablet is offered
10. Document heart rate, end tidal $CO_2$ level, and oxygen saturation on Capnic Challenge Form At the end of the test, the patient is provided half of an effervescent tablet and is told to chew on it while breathing through mouth and out of nose a few times. Additional effervescent tablets are given to the patient until the end tidal $CO_2$ level returns to baseline. Obtain final blood pressure and end tidal $CO_2$ level and record on Capnic Challenge form along with description of the changes in symptoms by the patient.

In some cases, a Capnic Challenge Test is performed with standing blood pressure challenge. In such cases, the test is performed as follows:
1. The patient sits, and blood pressure, heart rate, and pulse oximetry readings are obtained and recorded on the Capnic Challenge Form.
2). The patient is instructed to stand with two staff at stand-by (at each side of the patient). Blood pressure, heart rate, and pulse oximetry readings are obtained and recorded on the Capnic Challenge Form. After 30 seconds, blood pressure, heart rate, and pulse oximetry readings are obtained and recorded on the Capnic Challenge Form. After 60 seconds, blood pressure, heart rate, and pulse oximetry readings are obtained and recorded on the Capnic Challenge Form.
3). The patient is instructed to return to a sitting position. At 30 seconds, heart rate, end tidal $CO_2$ levels, and oxygen saturation are obtained and recorded on the Capnic Challenge Form. At 60 seconds, heart rate, end tidal $CO_2$ levels, and oxygen saturation are obtained and recorded on the Capnic Challenge Form. At 90 seconds, heart rate, end tidal $CO_2$ levels, and oxygen saturation are obtained and recorded on the Capnic Challenge Form.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A canister device for delivering breathing gas of oxygen and $CO_2$ to a mammal, wherein said canister device comprises an oxygen module, a $CO_2$ module, an actuator, and a mouthpiece, wherein said oxygen module comprises an oxygen gas source, wherein said $CO_2$ module comprises a liquid compartment for housing a liquid, a solid compartment for housing a solid, said liquid, and said solid, wherein said actuator is configured to allow said liquid to contact said solid upon actuation, thereby releasing $CO_2$ from said $CO_2$ module, wherein said actuator is configured to release oxygen from said oxygen module upon actuation, wherein said mouthpiece is in fluid communication with a $CO_2$ line connected to said $CO_2$ module and an oxygen line connected to said oxygen module, and wherein actuation of said actuator releases $CO_2$ and oxygen gas for said mammal to inhale through said mouthpiece.

2. The canister device of claim 1, wherein said mammal is a human.

3. The canister device of claim 1, wherein said liquid is an acid.

4. The canister device of claim 3, wherein said acid is ascorbic acid.

5. The canister device of claim 3, wherein said acid is acetic acid, tartaric acid, malic acid, or citric acid.

6. The canister device of claim 1, wherein said solid is a carbonate.

7. The canister device of claim 6, wherein said carbonate is sodium bicarbonate.

8. The canister device of claim 1, wherein said oxygen gas source is pressurized oxygen, molecular sieve derived oxygen, or liquid oxygen.

9. A method for treating a mammal suffering from hypocapnia, wherein said method comprises delivering breathing gas of oxygen and $CO_2$ to said mammal for said mammal to inhale through a mouthpiece of a canister device, thereby treating said hypocapnia, wherein said canister device comprises an oxygen module, a $CO_2$ module, an actuator, and said mouthpiece, wherein said oxygen module comprises an oxygen gas source, wherein said $CO_2$ module comprises a liquid compartment for housing a liquid, a solid compartment for housing a solid, said liquid, and said solid, wherein said actuator is configured to allow said liquid to contact said solid upon actuation, thereby releasing $CO_2$ from said $CO_2$ module, wherein said actuator is configured to release oxygen from said oxygen module upon actuation, wherein said mouthpiece is in fluid communication with a $CO_2$ line connected to said $CO_2$ module and an oxygen line connected to said oxygen module, and wherein actuation of said actuator releases $CO_2$ and oxygen gas for said mammal to inhale through said mouthpiece.

10. The method of claim 9, wherein said mammal is a human.

11. The method of claim 9, wherein said liquid is an acid.

12. The method of claim 11, wherein said acid is ascorbic acid.

13. The method of claim 11, wherein said acid is acetic acid, tartaric acid, malic acid, or citric acid.

14. The method of claim 9, wherein said solid is a carbonate.

15. The method of claim 14, wherein said carbonate is sodium bicarbonate.

16. The method of claim 9, wherein said oxygen gas source is pressurized oxygen, molecular sieve derived oxygen, or liquid oxygen.

* * * * *